United States Patent [19]

Tominaga

[11] 3,980,078

[45] Sept. 14, 1976

[54] ENDOSCOPE WITH CLEANING DEVICE

[75] Inventor: Hiroshi Tominaga, Omiya, Japan

[73] Assignee: Fuji Photo Optical Co., Ltd., Omiya, Japan

[22] Filed: July 22, 1975

[21] Appl. No.: 598,047

[30] Foreign Application Priority Data

July 23, 1974 Japan............................ 49-87509[U]

[52] U.S. Cl.................................... 128/4; 128/240; 128/276
[51] Int. Cl.²............................................. A61B 1/00
[58] Field of Search..................... 128/4–9, 128/275–278, 240, 241, 297–300; 32/69; 15/320–322, 250, 250.01, 250.02

[56] References Cited
UNITED STATES PATENTS

| | | |
|---|---|---|
| 3,109,426 | 11/1963 | Noonan et al....................... 128/276 |
| 3,643,653 | 2/1972 | Takahashi et al.................... 128/6 |
| 3,903,877 | 9/1975 | Terada.................................. 128/6 |
| 3,926,192 | 12/1975 | Van Maren.......................... 128/276 |

*Primary Examiner*—Robert W. Michell
*Assistant Examiner*—Henry S. Layton

[57] ABSTRACT

An endoscope having a cleaning device including an injection nozzle and a suction port is provided with drain ports at the marginal portion of its end face. The end of the endoscope is provided with a removable hood. The drain ports are formed between the hood and the end of the endoscope and communicated with the suction conduit in the endoscope body. The drain ports may be formed either on the periphery of the end part of the endoscope or on the internal face of the hood.

5 Claims, 4 Drawing Figures

ENDOSCOPE WITH CLEANING DEVICE

BACKGROUND OF THE INVENTION

1. Field of the Invention

This invention relates to an endoscope for examination of internal faces of body cavities, and more particularly to an endoscope having a cleaning device for cleaning the viewing window of the endoscope after insertion into a body cavity. The endoscope in accordance with the present invention is of the type in which a demountable hood is provided at the end thereof.

2. Description of the Prior Art

It has been known in the art to provide a cleaning device on an endoscope which is inserted into body cavities for examination of the internal faces thereof. The endoscope is usually comprised of an objective lens system, an image transmitting fiber optical tube, an eyepiece lens system and an illumination system to illuminate the internal faces of the body cavities into which the endoscope is inserted. The cleaning device is usually comprised of an injection nozzle provided near the viewing window at the end of the endoscope, an air and water transfer conduit extending through the endoscope along the image transmitting tube and a suction pipe extending through the endoscope along said tube and having an open end at the end of the endoscope. Cleaning water and/or air is supplied on the viewing window of the endoscope in the body cavity to clean the surface of the viewing window glass and is taken out of the body cavity through the suction pipe. The suction pipe usually has a single open end at the front end of the endoscope since the structure of the endoscope does not allow the suction pipe to have more than one opening at the end of the endoscope.

The above described endoscope with a cleaning device has a defect in that the drainage cannot be conducted efficiently when the open end of the suction pipe is positioned at a higher level than the injection nozzle. Therefore, when using the cleaning device of the endoscope, the operator must be careful to keep the open end of the suction pipe at a lower level than the injection nozzle.

It has also been known in the art to mount a hood at the end of an endoscope to keep the viewing window glass off the internal faces of the body cavity. The endoscope with the cleaning device and the hood is disadvantageous in that the cleaning water and liquid in the body cavity are likely to stay within the hood and hinder the observation of the internal faces through the viewing window.

SUMMARY OF THE INVENTION

In view of the above described defects inherent in the conventional endoscope, the primary object of the present invention is to provide an endoscope with a cleaning device in which the drainage of the cleaning water and other liquid in the body cavity which hinder the observation of the body cavity are effectively conducted out of the cavity.

Another object of the present invention is to provide an endoscope having a demountable hood and a cleaning device in which the cleaning water and other liquid in the body cavity are effectively drained and a clear image is always observed.

The endoscope in accordance with the present invention is characterized in that drain ports are provided around the front face of the endoscope. The drain ports are communicated with the suction pipe through grooves and holes.

DESCRIPTION OF THE PREFERRED EMBODIMENTS

Figure 1:
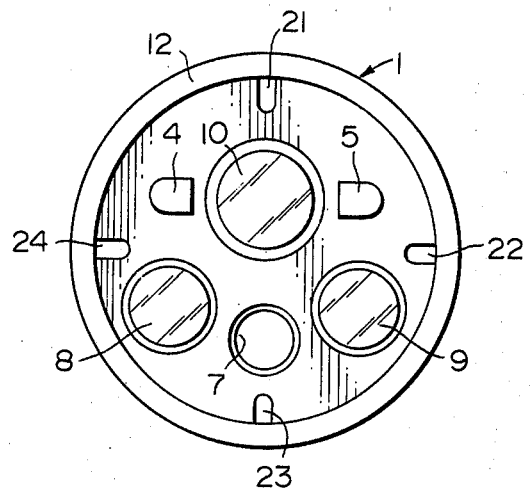
FIG. 1 is a front view of the end of the endoscope in accordance with the present invention.
Figure 2:
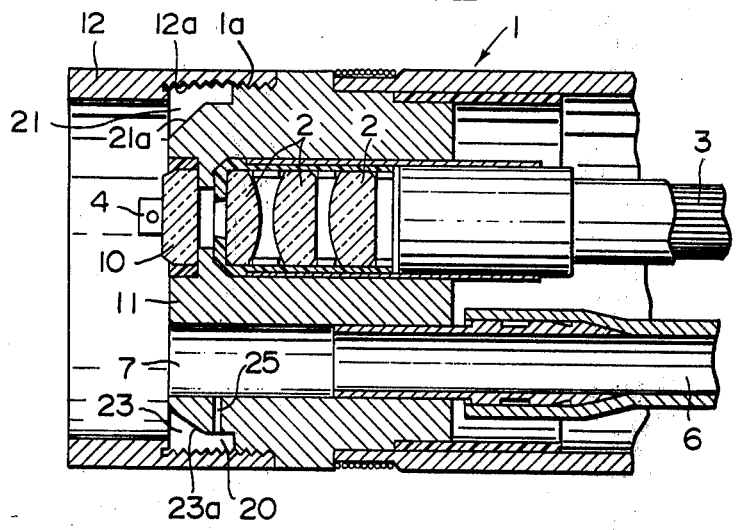
FIG. 2 is a longitudinal sectional view of the end part of the endoscope in accordance with the present invention.
Figure 3:
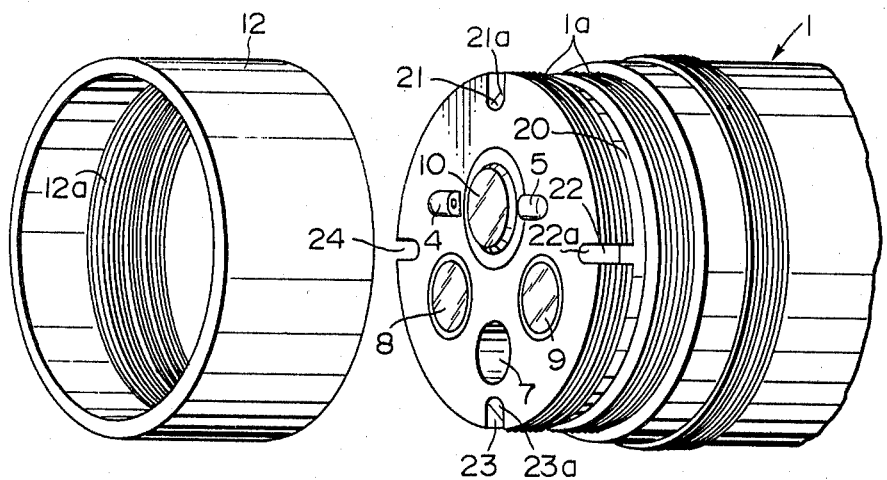
FIG. 3 is a perspective view showing the end part of the endoscope in accordance with the present invention.

An embodiment of the present invention is illustrated in FIGS. 1 to 3. Referring to FIGS. 1 to 3, a body 1 of the endoscope includes an objective lens system 2 located in front of a fiber optical light transmitting bundle 3, an air and water transfer conduit (not shown) having injection nozzles 4 and 5, a suction conduit 6 having an open drain port 7 and an illuminating system (not shown) having illumination window glasses 8 and 9. In front of the objective lens system 2 is located a viewing window glass 10. The viewing window glass 10, the illumination window glasses 8 and 9 and the drain port 7 are on the end face 11 of the body 1 of the endoscope. The injection nozzles 4 and 5 are located on the end face 11 directed to the surface of the viewing window glass 10.

The body 1 of the endoscope is provided on the outer periphery at the end thereof with a male screw 1a to which a female screw 12a provided on the inner periphery of a hood 12 is screwed.

The above described structure of the endoscope is the same as that of the conventional endoscope. The endoscope of the present invention is characterized in the structure as described hereinbelow.

Several drain ports 21, 22, 23 and 24 are provided at the marginal portion of the end face 11 of the endoscope. The drain ports 21, 22, 23 and 24 are communicated with said suction conduit 6 by way of longitudinally extending grooves 21a, 22a, 23a and 24a (not shown), a peripheral groove 20 provided around the body 1 of the endoscope in the vicinity of the end face 11 thereof and a through hole 25 radially extending from the peripheral groove 20 to the suction conduit 6. The drain ports 21, 22, 23 and 24 are formed in cutaway shape at the marginal portion of the end face 11 of the endoscope. When a hood 12 is mounted to the end of the endoscope, the drain ports 21, 22, 23 and 24 and the longitudinally extending grooves 21a, 22a . . . are covered by the hood 12 together with the peripheral groove 20 as shown in FIGS. 1 and 2.

In operation of the above described endoscope having said drain ports 21, 22, 23 and 24 in addition to the drain port 7, the cleaning water and other liquid in the body cavity in front of the end of the endoscope are effectively drained through the drain ports 21, 22, 23 and 24 since the drain ports 21, 22, 23 and 24 are provided at the marginal portion of the end face 11 of the endoscope. More exactly, the liquid in front of the end face 11 of the endoscope is drained through whichever of the four drain ports 21 to 24 is at the lowest level in the body cavity. The drain ports 21 to 24 are capable of draining the liquid in the body cavity even when the hood 12 is not mounted to the end of the endoscope though the effect thereof is lower in this case.

Figure 4:
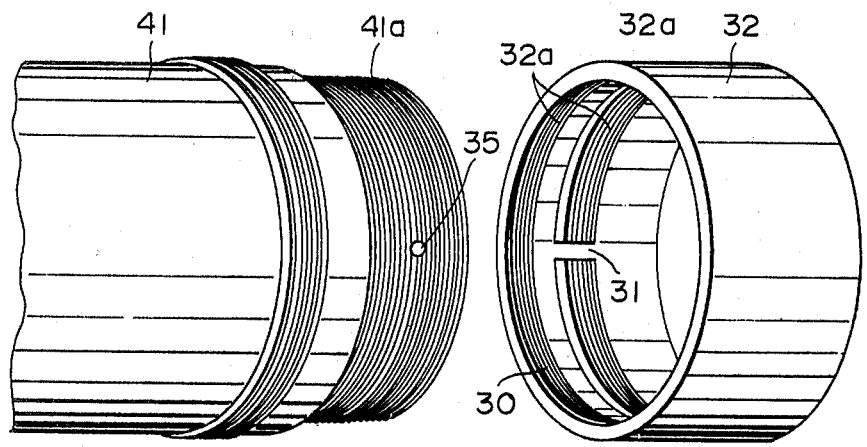
FIG. 4 is a perspective view showing the end part of the endoscope in accordance with another embodiment of the present invention.

A second embodiment of the present invention is illustrated in FIG. 4. In this embodiment, the drain ports are not provided on the marginal portion of the end face of the endoscope but are provided on the internal face of the hood. Referring to FIG. 4, longitudinally extending drain grooves, one of which is indicated at 31, are provided on the internal face of the hood 32. The internal face of the hood 32 is also provided with a peripheral groove 30. The outer periphery of the endoscope body 41 is provided at the end part thereof with a male screw 41a and is screw engaged with a female screw 32a provided on the internal face of the hood 32. The endoscope body 41 is provided with a through hole 35 extending from the surface of the male screw 41a to the suction conduit (not shown) therein at a position to be engaged with said peripheral groove 30 on the internal face of the hood 32.

In operation of the endoscope as described hereinabove and shown in FIG. 4, the cleaning water and other liquid in the body cavity in front of the end face of the endoscope are drained through said drain grooves, said peripheral groove 30, said through hole 35 and said suction conduit.

It will be noted that any number of drain ports may be formed at the marginal portion of the end face of the endoscope and that the drain ports may be formed into a single peripheral groove, a configuration which is equivalent to that obtained by increasing the number of ports until adjacent ports interconnect. The ports should preferably be in the form of separated groove-like ports as shown in the first and second embodiments, since in this case the suction force is much higher than when the ports are formed into a single peripheral groove.

Further, it will be understood that the suction port or the drain port open at the end of the suction conduit in this invention can be used as a guide tube for guiding forceps for collecting cells in the body cavity since there are provided several drain ports beside the suction port.

I claim:

1. An endoscope with a cleaning device wherein an air and water transfer conduit and a suction conduit are provided in the body of the endoscope, and having an end face provided with an injection nozzle and a suction port, and a hood is demountably mounted to the end of the endoscope, characterized in that a drain port means is formed between the hood and the marginal portion of the end face of the endoscope, and drain port means being communicated with said suction conduit.

2. An endoscope with a cleaning device as claimed in claim 1 wherein said drain port means comprises a plurality of drain ports located at equal intervals around the end face of the endoscope.

3. An endoscope with a cleaning device as claimed in claim 2 wherein said drain ports are communicated with the suction conduit by way of longitudinally extending grooves directly connected with the drain ports and a peripheral groove communicated with all the longitudinal grooves and at least one through hole extending from said peripheral groove to said suction conduit.

4. An endoscope with a cleaning device as claimed in claim 3 wherein said drain ports, said longitudinally extending grooves and said peripheral groove are formed on the outer face of the endoscope.

5. An endoscope with a cleaning device as claimed in claim 3 wherein said drain ports, said longitudinally extending grooves and said peripheral groove are formed on the inner face of the hood.

* * * * *